US005801011A

United States Patent [19]

Gardner

[11] Patent Number: 5,801,011
[45] Date of Patent: Sep. 1, 1998

[54] PROCESS FOR PREPARING CEPHALOSPORINS WITH PENICILLIN ACYLASE WITHOUT PH CONTROL

[75] Inventor: John P. Gardner, Indianapolis, Ind.

[73] Assignee: Eli Lilly and Company, Indianapolis, Ind.

[21] Appl. No.: 588,148

[22] Filed: Jan. 18, 1996

Related U.S. Application Data

[63] Continuation of Ser. No. 210,652, Mar. 21, 1994, abandoned, which is a continuation of Ser. No. 874,257, Apr. 24, 1992, abandoned.

[51] Int. Cl.$^6$ .................................................. C12P 35/00
[52] U.S. Cl. ........................... 435/47; 435/43; 435/195; 435/230; 435/231
[58] Field of Search .......................... 435/47, 43, 195, 435/230, 231

[56] References Cited

U.S. PATENT DOCUMENTS

| 3,816,253 | 6/1974 | Takahashi | 435/47 |
| 4,113,566 | 9/1978 | Hamsher . | |

FOREIGN PATENT DOCUMENTS

| 0473008 A2 | 3/1992 | European Pat. Off. . |
| A-2132271 | 11/1972 | France . |
| A-2-134530 | 12/1972 | France . |
| A-2255379 | 7/1975 | France . |
| A-640240 | 12/1983 | Switzerland . |
| 1348359 | 3/1974 | United Kingdom . |
| 1385943 | 3/1975 | United Kingdom . |
| 1482481 | 8/1977 | United Kingdom . |

OTHER PUBLICATIONS

Nam et al., *Biotechnology and Bioengineering*, 27, 953–960 (Jul. 1985).
Kang et al., *Korean J. of Appl. Microbiol. Bioeng.*, 15, No. 3, 203–208 (1987).
Kasche, *Biotechnology Letters*, 7, No. 12, 877–882 (1985).
Kasche, *Enzyme Microb. Technol.*, 8, 4–16 (Jan. 1986).
Savidge, *Drugs and Pharm. Sci.*, 22, 171–224 (1984).
Takahashi et al., *Journal of the Amer. Chem. Soc.*, 94, No.11, 4035–4037, (1972).
Okachi et al., *Enzyme Eng.*, 6, 81–90 (1982).
Baldaro, "Effect of Temperature on Enzymatic Synthesis of Cephalosporins", *Bioorg. Chem. in Healthcare and Technology*, vol. 207, pp. 237–240 (1991).
Marconi et al, *Agric Biol. Chem.*, vol. 39 (1) pp. 277–280, 1975.
Choi et al, *Biotechnol. Bioeng.*, 1981, vol. 23 pp.361–371.

*Primary Examiner*—Irene Marx
*Attorney, Agent, or Firm*—Janet T. McClain; James J. Sales

[57] ABSTRACT

The invention relates to an improved process for preparing cephalosporins by reaction compounds such as 7-aminocephalosporanic acid, 7-amino-3-deacetoxycephalosporanic acid or their derivatives with derivatives of α-amino acids in the presence of a properly immobilized penicillin acylase enzyme under the following conditions, independently, or in combination: (1) at a temperature ranging from 0° C. to +20° C.; or (2) at ambient pH; with a high molar ratio of α-amino acid to a cephalosporanic nucleus.

11 Claims, No Drawings

PROCESS FOR PREPARING CEPHALOSPORINS WITH PENICILLIN ACYLASE WITHOUT PH CONTROL

This application is a continuation of application Ser. No. 08/210,652, filed on Mar. 21, 1994, now abandoned, which is a continuation of application Ser. No. 07/874,257, filed on Apr. 24, 1992, now abandoned.

FIELD OF THE INVENTION

The present invention relates to an industrially advantageous improved enzymatic process for the preparation of cephalosporins by condensing the corresponding 7-amino cephalosporin nucleus with an α-amino acid.

BACKGROUND OF THE INVENTION

An enzymatic process for the preparation of cephalosporins by condensation of an amino acid derivative and an 7-amino cephalosporin nucleus is described in U.S. Pat. No. 3,816,253. In most of the examples of this patent, the microorganisms which produce the enzyme are themselves added to the reaction mixtures as the enzyme source. A crude cell-free preparation and a preparation that has been subjected to two chromatography steps are also exemplified. The patent describes a 5° to 50° C. temperature range for carrying out the reaction, with a 20° to 40° C. range being most advantageous. However, in all but one of the examples, the reaction is carried out at 37° C. In the sole exception, the reaction is carried out at 25° C. and achieves a reported 63% yield.

When operating at the temperatures exemplified in the above patent, the yield of the desired product can be reduced by competing reactions which cause the formation of contaminating by-products, primarily a hydrolysis product of the amino acid derivative. These by-products cannot always be easily separated from the reaction mixture. However, irrespective of how easily the by-products can be removed, their presence increases the cost of production.

As the enzymatic process has been applied in the past, substantial amounts of enzyme are consumed with each synthesis reaction. Thus, the cost of the enzyme is a substantial part of the cost of the process.

Due to the current cost of operating the enzymatic process, it is not as commercially attractive as a conventional organic chemical process. However, the enzymatic process has a number of advantages over the organic chemical process that would be more important commercially if the cost of the enzymatic process were reduced. For instance, the enzymatic reaction process requires only one reaction step, while the organic chemical process requires several steps. Further, the organic chemical process is lengthy, uses substantial amounts of solvents such as pyridine and creates unwanted by-products.

In view of the above, what is needed in the art is an enzymatic process that achieves yields as good as or better than those previously achieved enzymatically.

SUMMARY OF THE INVENTION

It has now been found that it is possible to increase the yield of the desired cephalosporin antibiotic product to higher levels than disclosed by prior art by carrying out a condensation reaction (as described below) at temperatures ranging from +20° C. to 0° C. in the presence of immobilized penicillin acylase in a suitable reaction medium/solvent.

Another aspect of the process of the invention is directed to carrying out the condensation such that the pH is allowed to remain ambient, as defined hereinbelow.

A further aspect of the process of the invention is directed to carrying out the condensation using a high α-amino acid to cephalosporin nucleus molar ratio.

DESCRIPTION OF THE INVENTION

The process of the invention can be used to prepare cephalosporins of formula (I):

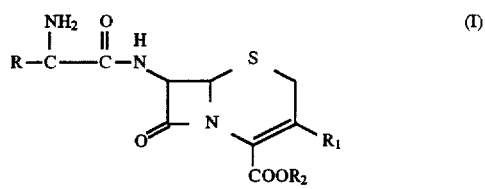

wherein R is a five- or six-membered hydrocarbon ring optionally substituted, or R is a five-membered heterocycle containing one to four heteroatoms (N, O or S), which heterocycle may be optionally substituted; $R_1$ is hydrogen, halogen, methyl, a methoxy or a methylene group bonded to an organic radical, the methylene optionally bonded to the radical via a bridging oxygen, sulphur or nitrogen atom; and $R_2$ is hydrogen or a carboxy protecting group.

This process comprises reacting a reactive derivative (the derivation occurring via the substitution of the hydroxy group of the carboxy moiety) of an α-substituted α-amino acid of formula (III):

with an 7-amino cephalosporin substrate compound of formula (II):

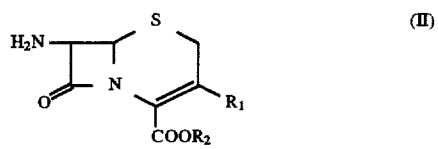

wherein R, $R_1$ and $R_2$ are the groups previously described, in the presence of a penicillin acylase enzyme, which is preferably immobilized, independently at a temperature ranging from 0° C. to +20° C., preferably 0° C. to 5° C.; or at ambient pH; or at a high α-amino acid to cephalosporin substrate molar ratio.

The prior art enzymatic production of cephalosporins is characterized by the production of contaminating by-products and loss of enzyme during the production process. In a first embodiment of the present invention, the quantity of contaminants arising during production of these antibiotic compounds by employing a condensation reaction between a reactive derivative of an α-substituted α-amino acid of formula (III) with an 7-amino cephalospoprin substrate of formula (II) in the presence of an immobilized enzyme at a temperature ranging from about 0° C. to about 20° C. is reduced.

At low temperatures, the activity of enzymes is generally depressed, often markedly so. To meet this problem the present invention generally uses greater amounts of enzyme. By this approach, favorable product yields are achieved at very low temperatures, e.g., 0° C. to 50° C.

In the practice of this bio-catalytic condensation process, a maximum product concentration is achieved after a period of time which varies based on enzyme amount, substrate, temperature, and other variables which will be known to those of ordinary skill in the art. Thereafter, the concentration of product remains constant for a period of time approximately proportional to the time required to achieve maximum product concentration. For instance, if the maximum product concentration is achieved in about two hours, the plateau concentration lasts for about one hour. Afterwards, the product concentration usually decreases. In practicing the invention, it is preferred to employ that quantity of penicillin acylase enzyme that results in a stable product concentration (or plateau concentration) that lasts for about one hour so that there is enough time to remove the product from the reactor. However, a plateau period of between about 10 min. and about 120 min., more preferably between about 30 and about 80 min., should be useful in practicing the invention.

In another embodiment of the invention, the pH is allowed to remain ambient, or, in other words, is not kept constant by means such as a buffered solution. Ambient pH conditions are those in which the pH is allowed to drift or change without intervention during the reaction. Normally, the pH is set at about 7–7.5 and is allowed to drop during the reaction to a pH of 6–7. While not wishing to be bound by theory, it is believed that under ambient pH, the hydrolysis of PGME and the final product are reduced compared with the rate of formation of the final product.

Generally, in all embodiments of the invention, the amount of enzyme used is 50–3000 IU enzyme per gram of 7-amino cephalosporin substrate (II). Of course, it will be recognized by those of ordinary skill in the art that the amount of enzyme favorably used in the process will vary, for instance, with the nature and quality of the substrate, with the scale of the reaction, with the temperatures used, and with the type of apparatus used.

With respect to the above formulas, R may be: a five- or six-membered aliphatic or aromatic hydrocarbon ring (e.g., phenyl, cyclohexadienyl, cyclohexenyl or cyclohexyl) optionally substituted with one or more radicals including but not limited to hydroxyl, halogen, alkyl, alkoxyl, carboxyl, nitro, amino, and the like; or it can be a five-membered heterocycle containing one or more heteroatoms (preferably no more than four) selected from O, N and S or combinations thereof (e.g., thienyl, furyl, and the like), which heterocycle may be substituted by one or more radicals (preferably no more than three) including but not limited to hydroxyl, halogen, alkyl, alkoxyl, carboxyl, nitro, amino, and the like. Particularly preferred are product compound (I) and corresponding formula (III) compounds where R is an unsubstituted phenyl, a p-hydroxyphenyl, or a 1,4-cyclohexadien-1-yl radical.

When R is a heterocyclic radical, it is anticipated that the 4-thiazolyl, furyl and thienyl radicals can be advantageously employed.

$R_1$, in turn, can be a hydrogen atom, a halogen atom (Br, Cl, I, F), a methoxy, a methyl or a methylene bonded to an organic radical such as a $C_1$–$C_6$ alkoxy, a $C_1$–$C_6$ alkoxycarbonyl or a five-or six-membered heterocyclic group containing one to four heteroatoms selected from O, S and N or combination thereof, the methylene group being optionally bonded to the radical via a bridging atom of O, S or N, the heterocyclic group may also optionally bear substituents such as one or more radicals including (without limitation): hydroxy, halogen, $C_1$–$C_6$ alkyl, $C_1$–$C_6$ alkoxy, carbonyl, carboxy, cyano, amino, nitro and the like. Particularly preferred $R_1$ are methyl, methoxy, chloro, and acetoxymethylene. Preferred heterocyclic radicals for $R_1$ (exclusive of the methylene and heteroatom by which the heterocycle may be attached to the lactam ring system) are the 1H-1,2,3-triazol-4-yl, 1H-tetrazol-5-yl and 2-thiazolyl radicals.

The reactive derivatives of α-substituted α-amino acids which can be used in the invention are those derivatives at the carboxyl moiety wherein the hydroxy of the carboxylic moiety has been substituted with an organic group which can be hydrolyzed to re-create the carboxylic acid by exposure to the penicillin acylase which is to be employed in the condensation. While not wishing to be bound by theory, it is believed that this experiment identifies those derivatives which can react with the enzyme to form a reactive acyl-enzyme intermediate which can then react and form an amidic bond with the 7-amino cephalosporin nucleus of formula (II).

Useful examples of reactive derivatives of the α-amino acid of formula (III) are alkyl esters (e.g. methyl esters, ethyl esters), aralkyl esters (e.g. benzyl esters), amides and dipeptides (i.e., amides formed with a second amino acid). The methyl esters of D-phenyglycine, D-p-hydroxyphenylglycine, and D-1,4-cyclohexadien-1-yl-glycine are preferred examples. Other examples of carboxy protecting groups ($R_2$) may be found in U.S. Pat. No. 4,892,942, or E. Haslam, *Protective Groups in Organic Chemistry*, J. G. W. McOmie, Ed., Plenum Press, N.Y., N.Y., 1973, Chapter 5, and T. W. Greene, *Protective Groups in Organic Synthesis*, John Wiley & Sons, N.Y., N.Y., 1981, Chapter 5, herein incorporated by reference.

The following acids are of particular interest among the compounds of formula (II): 7-amino-cephalosporanic acid, 7-amino-3-deacetoxy-cephalosporanic acid, and 7-amino-3-chloro-cephalosporanic acid.

The penicillin acylase enzyme used in the process according to the present invention may be derived from any of the known microbial sources. Among these are micro-organisms of the Xanthomonas, Pseudomonas, Aeromonas, Escherichia, Arthrobacter, Corynebacterium and Bacillus genera.

The use of penicillin acylase derived from *Escherichia Coli* ATCC 9637 is particularly preferred.

The process according to the present invention is preferably carried out in the presence of an immobilized enzyme. The immobilization can be done by any one of a number of well-known immobilization techniques, such as: absorption, ionic or covalent bond to polymer matrices, cross-linking, trapping in gel or fibers, microencapsulation or entrapment behind an ultrafiltration membrane in a membrane reactor (i.e., membrane partition). Use of an enzyme incorporated into cellulose triacetate fiber structures or covalently bonded to polyacrylamidic resin is preferred.

Immobilized penicillin Acylase, either fiber entrapped or covalently bonded to a polymeric matrix is commercially available from Recordati, S.p.A., Biochemical Unit De.Bi., Cassina de Pecchi, Italy.

The compound of formula (II) is reacted in concentrations of about 0.5 to about 2% (wt/v), preferably 1.4 to 1.5%. In another embodiment of the invention, the reactive derivatives of formula (III) are reacted in high molar ratios (between about 3 to about 5) based on the amount of compound of formula (II).

While the reaction may be carried out at a temperature ranging from about 0° C. to about +20° C., temperatures in the range of 0° to 2° C. are preferred.

A preferred solvent system is water only. However, suitable organic solvents include ethylene glycol, lower alcohols (e.g., methanol, ethanol, iso-propanol, 2-butanol), acetone and the like, which may be used in the aqueous system.

During the course of the reaction process according to the present invention, the extent of reaction and product quality may be monitored by high performance liquid chromatography (HPLC) and other known methods.

In a most preferred process, two of the advantageous variables, temperature and ratio, are controlled for maximum yield, and pH is allowed to remain ambient.

The following examples will better explain the characteristics and applicability of the invention, but will not limit its scope.

To illustrate the invention, 7-amino-3-chlorocephalosporanic acid ("7-ACCA") is used as the cephalosporin substrate. 7-ACCA can be prepared as described by R. R. Chauvette et al., *J. Med. Chem.* 18:403 (1975). D-phenylglycine methyl ester ("PGME") and D-p-hydroxyphenylglycine methyl ester ("HPGME") can be prepared from commercially available amino acids (e.g. from SIGMA) using standard esterification procedures such as treatment with methanol in the presence of HCl. This and other classical methods of derivatizing amino acids are described in *Survey of Organic Synthesis*, by C. A. Buehler and D. E. Pearson, Wiley-Interscience, New York, 1970, Vol 1, pp. 801–830 and in Vol. 2 (1977), pp. 711–726.

EXAMPLE 1

7-(D-2-ammonium-2-phenylacetamido)-3-chloro-3-cephem-4-carboxylate, inner salt

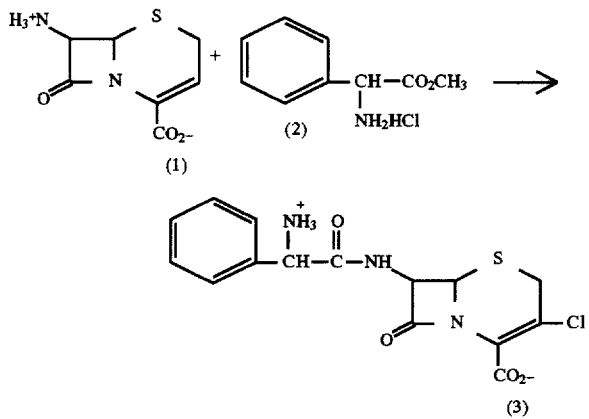

(1) 7-ACCA (1) (0.9388 g, 4.0007 mmol) and 96.0 ml of $H_2O$ are combined in a beaker. The pH is 4.12. Three molar $NH_3$ (1.78 ml) is added to the beaker. The pH is 7.57. D-phenylglycinemethyl ester hydrochloride (2) (4.7594 g, 23.602 mmol) is added to the beaker. The pH is 5.68. The mixture is cooled to 5° C., and three molar $NH_3$ (1.90 ml) is added to the mixture to raise the pH to 7.00. Enzyme (6.1442 g, 940 IU/g of nucleus) is added. The following reaction rate data, via HPLC analysis, is provided:

| Time (Min) | pH | Temp(°C.) | Compound 1 % remaining | Compound 2 % remaining | Compound 3 % formed |
|---|---|---|---|---|---|
| 0 | 7.00 | 6 | 100 | 100 | — |
| 85 | 6.28 | 5 | 9.2 | 67.1 | 91.4 |
| 120 | 6.16 | 4 | 9.1 | 64.3 | 91.5 |
| 180 | 5.97 | 4.5 | 8.9 | 63.7 | 91.8 |
| 200 | 5.91 | 4.5 | 8.8 | 65.3 | 93.0 |

At time=200 minutes, the mixture is filtered (to remove the immobilized enzyme) with an in situ yield of the titled product being 93%.

EXAMPLE 2

7-(D-2-ammonium-2-phenylacetamido)-3-chloro-3-cephem-4-carboxylate, inner salt (1) 7-ACCA (1.0072 g, 4.000 mmol) and purified $H_2O$ (550 ml) are combined in a beaker. The pH is 3.39. Three molar $NH_3$ (4.10 ml) is added to the mixture. The pH is 6.73. D-phenylglycine-methylester hydrochloride (4.8397 g, 24.000 mmol) is added to the mixture. The pH is 6.5. The mixture is diluted to 75.09 ml with $H_2O$ (13.77 ml). Wet enzyme (3.0672 g, ~470 IU/gm nucleus) is added to the mixture. (During experiment, the pH is adjusted up to 6.5 every 30 minutes). The following data is provided via HPLC:

| Time (Min) | pH | Temp(°C.) | Compound 1 % remaining | Compound 2 % remaining | Product % formed |
|---|---|---|---|---|---|
| 0 | 6.48 | 6 | 95.9 | 100 | — |
| 30 | 6.34 | 5.5 | 53.0 | 87.0 | 32.5 |
| 60 | 6.39 | 5.5 | 36.0 | 82.3 | 48.9 |
| 90 | 6.41 | 5 | 24.2 | 79.6 | 59.7 |
| 120 | 6.41 | 5.5 | 17.6 | 73.2 | 66.3 |
| 210 | 6.38 | 3.5 | 9.0 | 69.5 | 78.5 |
| 240 | 6.37 | 5 | 8.0 | 67.8 | 80.8 |
| 270 | 6.38 | 4.5 | 6.9 | 66.3 | 82.3 |
| 300 | 6.42 | 4.5 | 6.8 | 61.7 | 80.8 |
| 330 | 6.42 | 4.0 | 6.2 | 61.0 | 80.1 |
| 350 | 6.42 | 5 | 7.1 | 47.7 | 88.2 |

After 350 minutes, the mixture is filtered, with the in-situ yield of the titled product being 88.2%

EXAMPLES 3–17

7-(D-2-ammonium-2-phenylacetamido)-3-chloro-3-cephem-4-carboxylate, inner salt

For examples 3 to 17, the following general procedure is employed: (1) 7-ACCA (1.0072 g, 4.00 mmol) is combined with $H_2O$. The pH of the mixture is adjusted with three molar $NH_3$ to obtain a solution. A designated amount of D-phenylglycine methylester hydrochloride is added, as indicated in the table below. The mixture is cooled to 5° C. Three molar $NH_3$ is then added in an amount to obtain the pH as indicated in the Table below. The mixture is diluted with $H_2O$ to the concentration as designated in the Table below. Wet enzyme (3.07 g, 500 IU/gm nucleus) is then added. The pH is not adjusted except when the starting pH is 6.5, wherein the reaction pH is maintained between 6.2–6.5.

Reaction Conditions:
 a) 1.0 eq. D-phenylglycine methylester hydrochloride
 b) 3.5 eq. D-phenylglycine methylester hydrochloride
 c) 6.0 eq. D-phenylglycine methylester hydrochloride
 d) 0.5 concentration
 e) 1.25 concentration
 f) 2.0 concentration
 g) 6.5 starting pH (upon addition of enzyme)
 h) 7.25 starting pH (upon addition of enzyme)
 i) 8.0 starting pH (upon addition of enzyme)

| Example | Reaction Conditions | Time (Min.) | Product Yield |
|---|---|---|---|
| 3 | C,F,H | 150 | 86.9 |
| 4 | C,D,H | 150 | 80.6 |

-continued

| Example | Reaction Conditions | Time (Min.) | Product Yield |
| --- | --- | --- | --- |
| 5 | A,F,H | 275 | 46.6 |
| 6 | A,D,H | 180 | 28.9 |
| 7 | C,E,I | 60 | 83.4 |
| 8 | C,E,G | 330 | 84.7 |
| 9 | A,E,I | 45 | 34.3 |
| 10 | A,E,G | 540 | 42.8 |
| 11 | B,F,I | 60 | 79.8 |
| 12 | B,F,G | 360 | 78.9 |
| 13 | B,D,I | 60 | 56.2 |
| 14 | B,D,G | 630 | 70.8 |
| 15 | B,E,H | 180 | 80.4 |
| 16 | B,E,H | 190 | 81.0 |
| 17 | B,E,H | 180 | 80.8 |

EXAMPLE 18

7-(D-2-ammonium-2-phenylacetamido)-3-chloro-3-cephem-4-carboxylate, inner salt (1) 7-ACCA (4.8338 G, 20 mmol) is combined with $H_2O$ (150 ml). The pH is 3.67. Three molar $NH_3$ (8.40 ml) is added to the mixture. The pH is 8.20. D-phenylglycine methyl ester (23.0 g, 114 mmol) is added to the mixture. The pH is 5.29. The mixture is filtered through filteraid and diluted with 100 ml $H_2O$. The volume of solution is 310 ml. Water (5 ml) is added and the solution is cooled to 1° C. The pH is 5.80. The pH is adjusted to 7.28 with three molar $NH_3$ (16.6 ml). The volume is 332 ml. Water washed enzyme (15.34 g) is added. The following is provided, via HPLC analysis:

| Time (Min.) | pH | Temp (°C.) | Compound 1 % remaining | Compound 2 % remaining | Product % formed |
| --- | --- | --- | --- | --- | --- |
| 0 | 7.28 | 2 | 96.0 | 94.5 | — |
| 90 | 6.94 | 1 | 8.1 | 61.5 | 87.7 |
| 120 | 6.83 | 1 | 6.6 | 56.0 | 84.8 |
| 145 | 6.76 | 1 | 7.1 | 58.5 | 89.8 |

EXAMPLE 19

7-(D-2-ammonium-2-phenylacetamido)-3-chloro-3-cephem-4-carboxylate, inner salt (1) 7-ACCA (0.494 g, 2.000 mmol) and 42.0 ml of 0.0033M $K_2HPO_4$ pH 6.5 buffer are placed in a beaker. The pH is 5.91. To the solution, 45% $K_3PO_4$ (eq) (0.92 ml) is added to dissolve. The pH is 7.24. D-phenylglycine methylester hydrochloride (2.3797, 11.801 mmol) (2) is added. The pH is 6.40. 45% $K_3PO4$ (1.10 ml) is added to obtain a pH of about 7.0. Enzyme (2.6120 g, 800 IU/g nucleus) is added. At T=43 minutes, the pH is adjusted to 7.00 with 1.34 ml of 45% $K_3PO_4$. The maximum yield of the titled product is 66.1%.

| Time (Min.) | pH | Temp (°C.) | Compound 1 % remaining | Compound 2 % remaining | Product % formed |
| --- | --- | --- | --- | --- | --- |
| 0 | 6.95 | 0.25 | 93.6 | 95.1 | 0.0 |
| 5 | 6.72 | 26.5 | 32.0 | 66.8 | 54.8 |
| 10 | 6.62 | 27.5 | 20.6 | 55.7 | 64.0 |
| 15 | 6.50 | 28 | 17.6 | 48.8 | 66.1 |
| 20 | 6.36 | 28.5 | 16.6 | 42.8 | 64.5 |
| 25 | 6.27 | 28.5 | 16.6 | 40.3 | 64.5 |
| 30 | 6.18 | 29 | 17.0 | 37.9 | 64.1 |
| 35 | 6.10 | 29 | 17.0 | 36.6 | 64.8 |
| 40 | 6.03 | 29.5 | 17.3 | 34.2 | 61.6 |
| 45 | 6.95 | 29.5 | — | 30.6 | 59.9 |
| 50 | 6.84 | 29.5 | 24.5 | 22.8 | 53.7 |
| 55 | 6.75 | 30 | 27.3 | 17.9 | 49.1 |
| 60 | 6.68 | 60 | 29.1 | 14.3 | 45.2 |

EXAMPLE 20

7-(D-2-ammonium-2-phenylacetamido)-3-chloro-3-cephem-4-carboxylate, inner salt

The experiment of Example 19 is run except that 2.2707 g of dried enzyme (2660 IU/g nucleus) is used. No adjustment is made to pH during the reaction. The maximum yield is 67.5%.

| Time (Min.) | pH | Temp (°C.) | Compound 1 % remaining | Compound 2 % remaining | Product % |
| --- | --- | --- | --- | --- | --- |
| 0 | 7.00 | 23.5 | 99.6 | 99.4 | — |
| 5 | 6.95 | 24 | 62.7 | 80.8 | 275 |
| 10 | 6.88 | 25 | 40.2 | 74.1 | 49.0 |
| 15 | 6.85 | 25 | 30.1 | 68.6 | 58.5 |
| 20 | 6.78 | 25.5 | 22.2 | 63.7 | 63.7 |
| 25 | 6.71 | 26 | 18.0 | 58.5 | 66.1 |
| 30 | 6.65 | 26.5 | 16.8 | 55.6 | 67.5 |
| 35 | 6.59 | 27 | 15.5 | 51.7 | 66.8 |
| 40 | 6.54 | 27 | 15.5 | 49.8 | 66.5 |
| 45 | 6.49 | 27 | 16.7 | 46.3 | 65.5 |
| 50 | 6.44 | 27.5 | 16.2 | 44.8 | 64.8 |
| 55 | 6.38 | 27.5 | 16.2 | 42.8 | 63.5 |
| 60 | 6.34 | 28 | 16.2 | 41.4 | 63.2 |
| 180 | 5.75 | 27 | 17.4 | 32.7 | 50.8 |

EXAMPLE 21

7-(D-2-ammonium-2-phenylacetamido)-3-chloro-3-cephem-4-carboxylate, inner salt

The experiment as recited in Example 19 is ran with the following changes:

Compound 1 used: 0.4698 g, 2.002 mmol

Compound 2 used: 2.381 g, 11.8074 mmol 0.033 M$K_2HPO_4$/pH 6.5 buffer used: 44.0 ml 45% $K_3$ $PO_4$ used: 0.95 ml/1.06 ml Wet enzyme used: 8.1686 g, 2660 IU/g of nucleus The pH is adjusted to 7.00 with 1.37 ml of 45% $K_3PO_4$ at T=52 minutes.

The maximum yield is 65.6%.

| Time (Min.) | pH | Temp (°C.) | Compound 1 % remaining | Compound 2 % remaining | Product % formed |
| --- | --- | --- | --- | --- | --- |
| 0 | 7.00 | 23.5 | 95.7 | 95.6 | — |
| 5 | 6.72 | 24 | 19.9 | 51.9 | 61.9 |
| 10 | 6.45 | 25 | 17.1 | 40.9 | 65.6 |
| 15 | 6.26 | 25 | 17.8 | 36.2 | 65.6 |
| 20 | 6.11 | 25.5 | 18.1 | 32.4 | 63.5 |
| 25 | 5.99 | 26 | 18.7 | 31.3 | 62.2 |
| 30 | 5.88 | 26 | 19.5 | 30.4 | 62.7 |
| 35 | 5.81 | 26.5 | 19.7 | 29.6 | 61.9 |
| 40 | 5.73 | 26.5 | 20.0 | 28.9 | 61.1 |

-continued

| Time (Min.) | pH | Temp (°C.) | Compound 1 % remaining | Compound 2 % remaining | Product % formed |
|---|---|---|---|---|---|
| 45 | 5.66 | 27 | 20.1 | 28.3 | 59.5 |
| 50 | 5.61 | 27 | 20.6 | 28.5 | 60.4 |
| 55 | 6.90 | 27 | 29.6 | 17.6 | 49.2 |
| 282 | 6.16 | 28 | 74.1 | — | 0.9 |

EXAMPLE 22

7-(D-2-ammonium-2-phenylacetamido)-3-chloro-3-cephem-4-carboxylate, inner salt

7-ACCA (0.470 g, 2.0058 mmol) (1) and 48.0 ml of 0.033M $K_2HPO_4$ (pH 6.5 buffer) are placed in a beaker. The pH is 5.73. The beaker is placed in a bath at 20° C. 45% $K_3PO_4$ (1.06 ml) is added to dissolve. The pH is 7.21. D-phenylglycine methylester hydrochloride (2.3811 g, 11.8099 mmol) (2) is added to the solution. The pH is 6.60. 45% $K_3PO_4$ (0.71 ml) is added to result in a pH of 7.00. Wet enzyme (3.0727 g) is added. The maximum in situ yield of the product is 74.6%.

| Time (Min.) | pH | Temp (°C.) | Compound 1 % remaining | Compound 2 % remaining | Product % |
|---|---|---|---|---|---|
| 0 | 7.00 | 20.5 | 100 | 100 | — |
| 5 | 6.89 | 20.5 | 43.4 | 76.1 | 48.7 |
| 10 | 6.78 | 20.5 | 25.4 | 62.0 | 62.1 |
| 15 | 6.68 | 21 | 21.8 | 59.5 | 71.0 |
| 20 | 6.60 | 21 | 20.1 | 56.0 | 74.0 |
| 25 | 6.52 | 21 | 18.9 | 52.2 | 73.5 |
| 30 | 6.45 | 21 | 18.6 | 49.1 | 72.0 |
| 35 | 6.40 | 20.5 | 19.1 | 47.8 | 74.6 |
| 40 | 6.35 | 20.5 | 19.0 | 46.9 | 73.4 |
| 45 | 6.31 | 21 | 18.7 | 44.2 | 71.2 |
| 50 | 6.27 | 20.5 | 19.3 | 46.0 | 72.9 |
| 55 | 6.22 | 21 | 19.5 | 44.5 | 72.5 |
| 60 | 6.19 | 21 | 19.8 | 43.7 | 72.4 |

EXAMPLE 23

7-(D-2-ammonium-2-phenylacetamido)-3-chloro-3-cephem-4-carboxylate, inner salt

7-ACCA (0.4710 g, 2.0071 mmol) (1) and 48.0 ml of 0.033M $K_2HPO_4$ (pH 6.5) are added to a beaker. The pH is 6.02. 45% $K_3PO_4$ (0.98 ml) is added to dissolve. The pH is 7.34. D-phenylglycinemethylester hydrochloride (2) (2.3801 g, 11.803 mmol) is added to the solution. The pH is 6.58. The beaker is placed in a bath (20° C.). 45% $K_3PO_4$ (0.63 ml) is added to adjust the solution pH to 7.00. Wet enzyme (3.0738 g) is added. The maximum yield of the titled product is 70.1%. [note to table: for times from 5 minutes to 50 minutes, small portions of 45% $K_3PO_4$ are added 1 minute prior to the 5 minute period to bump the pH of the solution to about 7.00].

| Time (Min.) | pH | Temp (°C.) | Compound 1 % remaining | Compound 2 % remaining | Product % |
|---|---|---|---|---|---|
| 0 | 6.99 | 19.5 | 99.3 | 98.7 | — |
| 5 | 7.01 | 20 | 52.2 | 80.6 | 36.3 |
| 10 | 7.02 | 20 | 33.9 | 69.4 | 57.7 |
| 15 | 7.00 | 20 | 24.4 | 60.4 | 63.1 |
| 20 | 7.00 | 20 | 20.6 | 55.1 | 67.1 |
| 25 | 7.00 | 20 | 20.1 | 51.9 | 69.6 |
| 30 | 7.00 | 20 | 19.7 | 47.4 | 70.1 |
| 35 | 7.00 | 20 | 20.3 | 43.5 | 68.7 |
| 40 | 7.03 | 20 | 21.3 | 39.9 | 67.9 |
| 45 | 7.00 | 20 | 22.2 | 36.7 | 66.2 |
| 50 | 7.01 | 20 | 23.8 | 33.5 | 65.7 |
| 140 | 6.58 | 20 | 37.2 | 14.4 | 50.2 |
| 240 | 6.41 | 20 | 38.0 | 11.1 | 44.1 |

EXAMPLE 24

7-(D-2-ammonium-2-phenylacetamido)-3-chloro-3-cephem-4-carboxylate, inner salt

7-ACCA (0.4696 g, 2.0012 mmol) (1) and 48.0 ml of $H_2O$ are placed in a beaker. The pH is 3.5. The solution is cooled to 10° C. Three molar $NH_3$ (2.47 ml) is added. The pH is 7.10. D-phenylglycinemethylester-hydrochloride (2.3835 g, 11.8198 mmol) is added. The pH is 5.65. Three molar $NH_3$ (4.30 ml) is added. The pH is 7.00. Wet enzyme (3.0778 g, 1000 IU/g nucleus) is added. [At T=256 minutes, the pH is adjusted to 7.00 with 2.60 ml of 3M $NH_3$]. The maximum yield is 71.1%.

| Time (Min.) | pH | Temp (°C.) | Compound 1 % remaining | Compound 2 % remaining | Product % formed |
|---|---|---|---|---|---|
| 0 | 6.98 | 10 | 97.0 | 96.7 | — |
| 5 | 6.89 | 10 | 55.9 | 81.8 | 33.6 |
| 10 | 6.80 | 10 | 36.3 | 76.0 | 52.0 |
| 15 | 6.73 | 10 | 27.3 | 71.0 | 58.3 |
| 20 | 6.65 | 10 | 22.3 | 69.5 | 61.8 |
| 25 | 6.56 | 10 | 19.3 | 69.3 | 68.3 |
| 30 | 6.50 | 10 | 17.3 | 67.9 | 70.5 |
| 35 | 6.44 | 10 | 15.7 | 65.4 | 71.1 |
| 40 | 6.37 | 10 | 14.2 | 62.5 | 62.5 |
| 45 | 6.31 | 10 | 14.1 | 64.0 | 64.0 |
| 50 | 6.27 | 10 | 13.6 | 65.7 | 65.7 |
| 55 | 6.22 | 10 | 13.0 | 63.4 | 63.4 |
| 75 | 6.07 | 10 | 12.1 | 62.8 | 62.8 |
| 236 | 5.50 | 10 | 10.9 | 61.4 | 61.4 |
| 257 | 7.00 | 10 | 10.9 | 59.5 | 59.5 |
| 276 | 6.64 | 10 | 11.5 | 51.1 | 51.1 |
| 313 | 6.25 | 10 | 11.1 | 45.6 | 45.6 |

EXAMPLE 25

7-(D-2-ammonium-2-phenylacetamido)-3-chloro-3-cephem-4-carboxylate, inner salt

7-ACCA (0.4694 g, 2.0003 mmol) (1) and 48.0 ml of $H_2O$ are placed in a beaker. The pH is 3.25. The solution is cooled to 10° C. Three molar $NH_3$ (3.05 ml) is added. The pH is 7.08. D-phenylglycine methyl ester hydrochloride (2) (2.3809 g, 11.8069 mmol) is added. The pH is 5.40. Three molar $NH_3$ (7.24 ml) is added to result in a pH of 7.00. Wet enzyme (8.1840 g, 2670 IU/g nucleus) is added. [At T=37 minutes, three molar $NH_3$ (1.72 ml) is added to adjust the pH to 6.52. At T=298 minutes, three molar $NH_3$ (1.72 ml) is added to adjust the pH to 6.55). The maximum yield is 71.2%.

| Time (Min.) | pH | Temp (°C.) | Compound 1 % remaining | Compound 2 % remaining | Product % formed |
|---|---|---|---|---|---|
| 0 | 7.00 | 10 | 98.6 | 97.0 | — |
| 5 | 6.75 | 10 | 22.3 | 58.7 | 59.9 |
| 10 | 6.46 | 10 | 14.1 | 49.0 | 71.2 |
| 15 | 6.20 | 10 | 12.5 | 43.6 | 68.3 |
| 20 | 5.98 | 10 | 11.8 | 42.3 | 69.1 |
| 25 | 5.80 | 10 | 12.4 | 41.1 | 69.1 |
| 30 | 5.70 | 10 | 12.6 | 41.8 | 69.7 |
| 35 | 5.58 | 10 | 12.4 | 40.6 | 68.9 |
| 40 | 6.52 | 10 | 13.0 | 38.6 | 70.1 |
| 45 | 6.14 | 10 | 13.6 | 33.7 | 66.9 |
| 50 | 5.96 | 10 | 13.9 | 33.3 | 67.4 |
| 55 | 5.80 | 10 | 14.7 | 33.2 | 68.0 |
| 60 | 5.69 | 10 | 14.8 | 32.5 | 67.6 |
| 121 | 5.11 | 10 | 15.1 | 31.0 | 67.8 |
| 300 | 6.55 | 10 | 16.9 | 28.9 | 66.1 |

EXAMPLE 26

7-(D-2-ammonium-2-phenylacetamido)-3-chloro-3-cephem-4-carboxylate, inner salt

7-ACCA (1) (0.4698 g, 2.002 mmol) and 48.0 ml of $H_2O$ are added in a beaker. The pH is 3.46. Three molar $NH_3$ (3.50 ml) is added. The pH is 7.23. D-phenylglycine methyl ester hydrochloride (2) (2.3798 g, 11.8015 ml) is added. The pH is 5.48. The mixture is cooled to 5° C. Three molar $NH_3$ (4.33 ml) is added to adjust the pH to 7.00. Wet enzyme (3.0710 g, 1000 IU/g nucleus) is added (At T=295 minutes, 2.87 ml of three molar $NH_3$ is added to result in a pH of 7.00). The maximum yield is 79.5%.

| Time (Min.) | pH | Temp (°C.) | Compound 1 % remaining | Compound 2 % remaining | Product % formed |
|---|---|---|---|---|---|
| 0 | 7.03 | 5 | 95.3 | 94.8 | — |
| 5 | 6.82 | 5 | 34.6 | 74.3 | 55.2 |
| 30 | 6.63 | 6 | 19.8 | 67.4 | 67.8 |
| 45 | 6.49 | 5 | 15.3 | 64.0 | 69.9 |
| 80 | 6.20 | 5 | 12.0 | 62.3 | 73.6 |
| 105 | 6.06 | 5.5 | 11.4 | 62.0 | 74.6 |
| 120 | 6.04 | 4.5 | 10.9 | 61.0 | 73.8 |
| 150 | 5.92 | 5 | 10.8 | 60.6 | 75.9 |
| 180 | 5.81 | 6 | 10.7 | 61.7 | 77.0 |
| 215 | 5.73 | 5.5 | 10.2 | 59.9 | 74.3 |
| 240 | 5.69 | 5.5 | 10.4 | 62.1 | 75.9 |
| 270 | 5.63 | 6 | 10.4 | 62.2 | 76.3 |
| 300 | 6.96 | 6 | 10.3 | 58.9 | 76.4 |
| 330 | 6.61 | 5.5 | 10.5 | 52.8 | 79.5 |

What is claimed is:

1. A method for preparing a cephalosporin of formula (I):

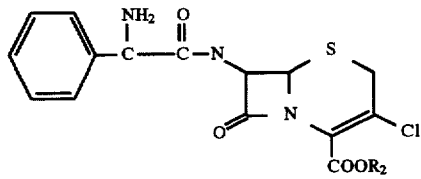 (I)

wherein $R_2$ is hydrogen or a carboxy-protecting group; comprising reacting a substrate of formula (II):

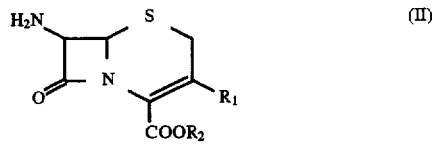 (II)

said substrate being present in a concentration of between about 0.5 to about 2% (wt/v); with a compound selected from D-phenylglycine methyl ester or D-phenyl glycine methyl ester hydrochloride, said compound being present in an amount of between about 3 to about 5 moles per mole of substrate; in the presence of 50–3000 IU of penicillin acylase enzyme per gram of substrate, and conducting said reaction at a temperature ranging from 0° C. to 2° C., where the pH is allowed to drift or change without intervention during the reaction, to produce a compound of formula I.

2. The method of claim 1, wherein said substrate is present in an amount of 1.4 to 1.5% (wt/v).

3. The method as recited in claim 1 wherein said penicillin acylase is produced by *Escherichia Coli* ATCC 9637.

4. A method for preparing a cephalosporin of formula (I):

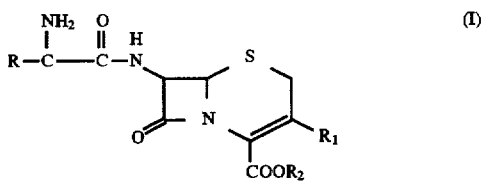 (I)

wherein:

R is phenyl;

$R_1$ is chloro; and $R_2$ is hydrogen or a carboxy-protecting group; comprising reacting a compound of formula (III):

 (III)

wherein the hydroxy of the carboxylic moiety has been substituted with methyl, ethyl or benzyl; with a cephalosporin substrate of formula (II):

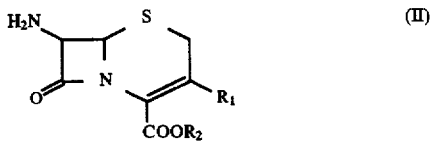 (II)

in the presence of an effective amount of a penicillin acylase enzyme and where the pH is allowed to drift or change without intervention during the reaction, to produce a compound of formula I.

5. The method of claim 4, wherein said enzyme is an immobilized penicillin acylase.

6. The method according to claim 5, wherein said compound of formula (III) is initially present in the reaction in an amount of 3 to 5 moles per mole of the cephalosporin substrate of Formula (II).

7. The method according to claim 4, wherein the compound of formula (III) is D-phenylglycine methyl ester and acceptable salts thereof.

8. The method according to claim 4, where the method is carried out at a temperature between about 0° C. and about 20° C.

9. The method according to claim 4, wherein the reaction temperature ranges from about 0° C. to about 5° C.

10. The method according to claim 4, wherein said pH is allowed to drift or change without intervention between a pH of about 5 to about 8.

11. The method according to claim 4, wherein said reacting occurs in a solution wherein water is the sole solvent.

* * * * *